(12) United States Patent
Hasson

(10) Patent No.: US 6,277,127 B1
(45) Date of Patent: Aug. 21, 2001

(54) SUPPORT AND MEDICAL INSTRUMENT COMBINATION

(76) Inventor: Harrith M. Hasson, 2043 N. Sedgwick, Chicago, IL (US) 60614

( * ) Notice: Subject to any disclaimer, the term of this patent is extended or adjusted under 35 U.S.C. 154(b) by 0 days.

(21) Appl. No.: 09/408,958

(22) Filed: Sep. 30, 1999

(51) Int. Cl.$^7$ .................................................. A61B 19/00
(52) U.S. Cl. ............................................................ 606/130
(58) Field of Search ....................... 606/1, 130; 248/121, 248/123.11, 125.2

(56) References Cited

U.S. PATENT DOCUMENTS

| | | | |
|---|---|---|---|
| 5,006,122 | * | 4/1991 | Wyatt et al. ........................ 606/130 |
| 5,047,036 | * | 9/1991 | Koutrouvelis ....................... 606/130 |
| 5,074,858 | * | 12/1991 | Ramos Martinez ................. 606/148 |
| 5,441,042 | * | 8/1995 | Putman ............................... 601/109 |
| 5,704,900 | * | 1/1998 | Dobrovolny et al. ............... 600/229 |

\* cited by examiner

Primary Examiner—Todd E. Manahan
Assistant Examiner—Eduardo C. Robert
(74) Attorney, Agent, or Firm—Wood, Phillips, VanSanten, Clark & Mortimer

(57) ABSTRACT

The combination of a medical instrument having a main body and a support. The support includes a base, a seating assembly on the base having a first seating surface against which the main body of the medical instrument abuts with the medical instrument in the operative position on the support, and a keeper assembly. The keeper assembly is mounted for guided movement relative to the base between a first position, wherein the keeper assembly maintains the medical instrument in the operative position, and a second position, wherein the medical instrument can be removed from the operative position.

14 Claims, 2 Drawing Sheets

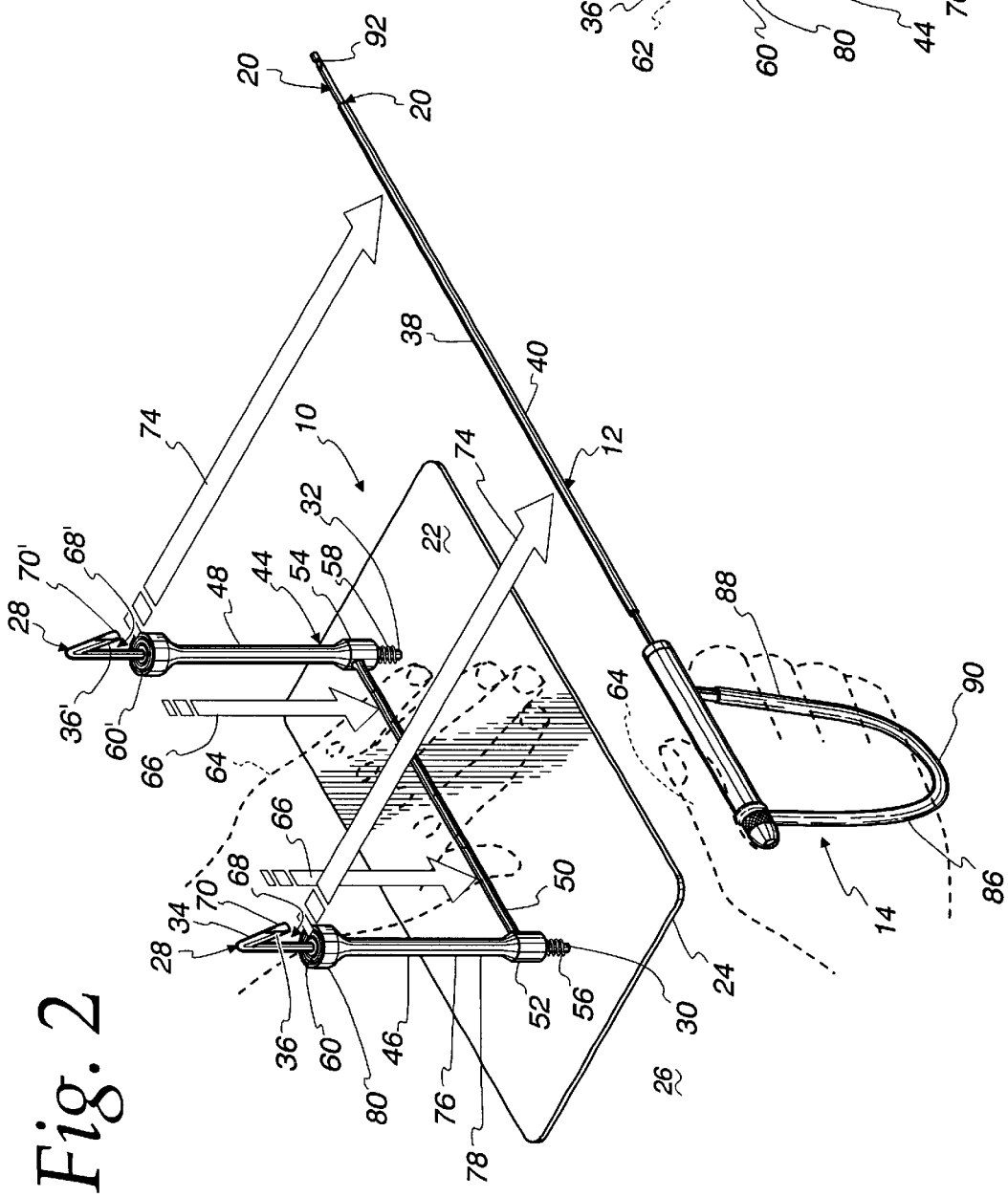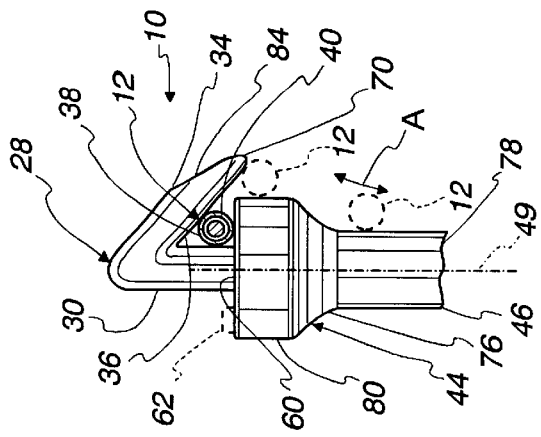

SUPPORT AND MEDICAL INSTRUMENT COMBINATION

BACKGROUND OF THE INVENTION

1. Field of the Invention

This invention relates to medical instruments and, more particularly, to a support on which a medical instrument can be releasably held in a predetermined orientation.

2. Background Art

It is common, during medical procedures, to place an object at the working end of a medical instrument. As an example, it is known to place a needle at the working end of an instrument in preparation for a suturing procedure. In my co-pending application (Ser. No. not assigned), there is disclosed a method of suturing involving the pre-forming of various knots at the working end of an instrument which can then be directed into a cavity for suturing at a desired site.

Manipulation of this type of instrument during these procedures may be awkward. This is particularly true of laparoscopic instruments which have a substantial length. The user may be required to attempt to hold the instrument with one hand and pre-form a knot, or perform whatever other step(s) is required at the working end, with the other hand. Alternatively, two sets of hands may be used to perform these procedures.

In any event, the instrument, whether held by one or two sets of hands, is inherently unstable, and the performance of intricate and delicate steps thereon may be difficult and relatively time consuming. This is contrary to the overriding objective of instrument designers to make instruments so as to facilitate the consistent performance of procedures therewith in a time efficient manner.

SUMMARY OF THE INVENTION

The invention is directed to the combination of a medical instrument, having a main body, and a support. The support includes a base, a seating assembly on the base having a first seating surface against which the main body of the medical instrument abuts with the medical instrument in the operative position on the support, and a keeper assembly. The keeper assembly is mounted for guided movement relative to the base between a first position, wherein the keeper assembly maintains the medical instrument in the operative position, and a second position, wherein the medical instrument can be removed from the operative position.

The base may include a flat surface which can be placed against a subjacent surface.

In one form, the first seating surface is fixed relative to the base.

In one form, the seating assembly includes a first post projecting from the base. The first seating surface is U-shaped. The keeper assembly includes a first body with a first shoulder that abuts to the medical instrument in the operative position, with the keeper assembly in the first position.

The first body and first post may be movable guidingly, one inside the other.

In one form, the seating assembly includes first and second posts each projecting from the base. The first seating surface is U-shaped. The seating assembly further includes a U-shaped second seating surface against which the main body of the medical instrument abuts with the medical instrument in the operative position on the support. The keeper assembly includes a first body with a first shoulder that abuts to the medical instrument in the operative position with the keeper assembly in the first position. A second body has a second shoulder that abuts to the medical instrument in the operative position with the keeper assembly in the first position.

In one form, a connector is connected between the first and second bodies so that the connector and first and second bodies move as one piece as the keeper assembly changes between the first and second positions.

In one form, the first body and first post and second body and second post are movable guidingly, one inside the other as the keeper assembly changes between the first and second positions.

The keeper assembly may be biased towards the first position. In one form, this bias is produced by a coil spring that surrounds the first post and acts between the base and the first body.

In one form, the first U-shaped seating surface opens in a first direction and the first body has an outer surface with a central axis and a diameter. The diameter of the outer surface varies smoothly so that the medical instrument can be guided against the outer surface oppositely to the first direction up to and past the first shoulder and against the first U-shaped seating surface.

In one form, the first U-shaped seating surface has a portion that extends radially from the central axis further than the outer surface at the first shoulder so that as the main body moves against the outer surface oppositely to the first direction up to and past the first shoulder, the main body encounters the portion of the first U-shaped surface.

The invention is also directed to a support for a medical instrument having a base, a seating assembly, and a keeper assembly. The base has a surface to facing in one direction to abut a surface upon which the support is placed. The seating assembly includes a first post projecting from the base and having a first U-shaped seating surface opening in the one direction and against which a medical instrument can be abutted with the medical instrument in an operative position on the support. The keeper assembly includes a first body with a first shoulder that is movable guidingly relative to the base between a first position, wherein the first shoulder, in conjunction with the first seating surface, cooperatively captively maintains a medical instrument in the operative position, and a second position, wherein a medical instrument can be placed in and removed from the operative position by movement relative to the first seating surface in the one direction and oppositely to the one direction.

In one form, the first body and first post are movable guidingly, one against the other, as the keeper assembly moves between the first and second positions.

The seating assembly may include a second post projecting from the base, with the keeper assembly including a second body, and the second post and second body are movable guidingly, one inside the other, as the keeper assembly moves between the first and second positions. The first and second posts each have a length, with the lengths of the first and second posts being substantially parallel to each other.

In one form, a connector connects between the first and second bodies so that the connector and first and second bodies move as one piece as the keeper assembly changes between the first and second positions.

The keeper assembly may be spring biased towards the first position. The connector may have a length sufficient to allow a user to place a plurality of fingers thereagainst and reposition the connector to thereby urge the keeper assembly towards the second position.

The invention is also directed to a method of using a medical instrument having a main body. The method includes the steps of: providing a support having a base, a seating assembly having a U-shaped seating surface, and a keeper assembly with a first shoulder that is movable guidingly relative to the base between first and second positions; placing the keeper assembly in the second position; directing the main body of the medical instrument against the seating surface to thereby place the medical instrument in an operative position; with the medical instrument in the operative position changing the keeper assembly into the first position so that the keeper assembly maintains the medical instrument in the operative position; and with the medical instrument maintained in the operative position, performing an operation on the medical instrument.

In one form, the medical instrument has a working end and the step of performing an operation includes one of a) forming a knot at the working end and b) placing an element at the working end.

BRIEF DESCRIPTION OF THE DRAWINGS

FIG. 2 is a view as in FIG. 1 with the support configured to allow the medical instrument to be separated therefrom; and FIG. 3 is a fragmentary, side elevation view of a portion of a seating assembly on the support and against which the medical instrument abuts with the medical instrument in the operative position therefor and with the medical instrument maintained in the operative position by a keeper assembly.

DETAILED DESCRIPTION OF THE DRAWINGS

Figure 1:
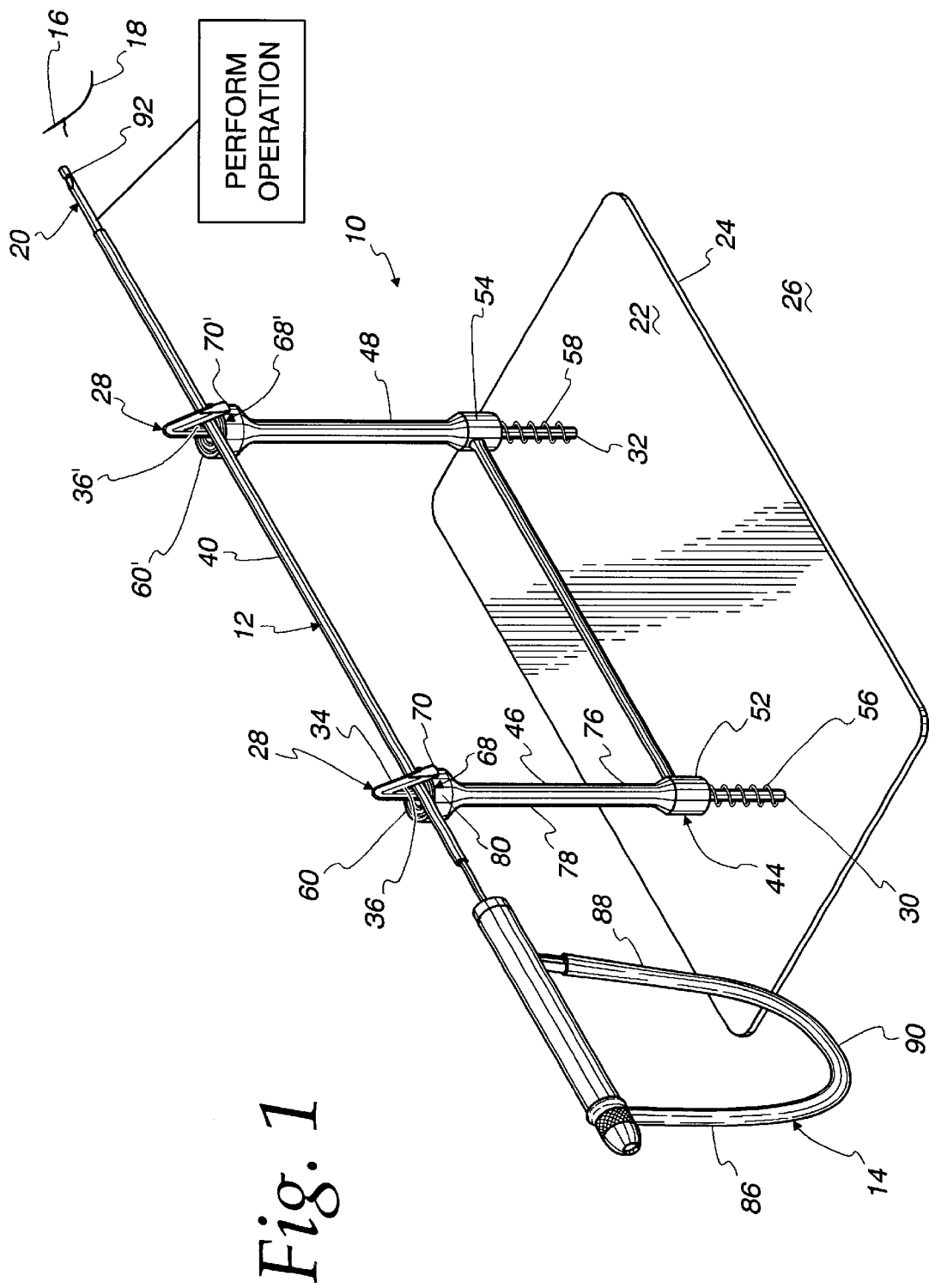
FIG. 1 is a perspective view of a medical instrument and a support therefor, according to the present invention, with the medical instrument shown in an operative position upon the support.

FIGS. 1–3 show a support at 10, according to the present invention, for a conventional medical instrument 12. The support 10 is intended to removably maintain the medical instrument 12 consistently oriented in an operative position, as shown in FIG. 1. In the operative position, the instrument 12 can be operated through a grip-type handle mechanism at 14 to facilitate placement of a suturing needle 16, carrying a thread 18, at a working end 20 of the instrument 12 remote from the handle mechanism 14. It is contemplated that virtually any type of operation can be performed by or on the working end 20, as indicated schematically in FIG. 1. For example, the working end 20 can be used to pre-tie a knot for introduction into a body cavity. Virtually any operation that can be performed through or on the medical instrument 12 can be facilitated using the support 10.

More specifically, the support 10 consists of a base 22, which has a flat plate with a flat bottom surface 24 for facially abutting a subjacent surface 26 upon which the support 10 is mounted. While in its simplest form the support 10 is situated on an upwardly facing surface, it could be mounted in virtually any orientation and function in the same manner.

The support 10 includes a seating assembly at 28 on the base 22 that consists of first and second posts 30, 32 that are fixed rigidly to, and project upwardly from, the base 22. The posts 30, 32 are elongate, with the lengths thereof being substantially parallel to each other.

The posts 30, 32 have the same construction. Representative post 30 has a bent end 34 which defines a downwardly opening U- or V-shaped seating surface 36 against which an outer surface 38 of a main body 40 of the medical instrument 12 abuts with the medical instrument 12 in the operative position.

A keeper assembly at 44 is mounted for guided movement relative to the base 22 between a first position, as shown in FIG. 1, wherein the keeper assembly 44 maintains the medical instrument 12 in the operative position, and a second position, as shown in FIG. 2, wherein the medical instrument 12 can be selectively placed in, and removed from, the operative position, by upward and downward movement of the medical instrument 12. The keeper assembly 44 consists of a first body 46 which surrounds the post 30 and a second body 48 which surrounds the post 32. With this arrangement, the first body 46 and post 30 reside one within the other and are guided one against and relative to the other along the lengthwise axis 49 of the post 30. The body 48 and post 32 cooperate in like fashion.

A connector 50 connects fixedly between the bodies 46, 48 and enlargements 52, 54 thereon. Through this arrangement, the entire keeper assembly 44, including the bodies 46, 48 and connector 50, moves as one piece between the first and second positions for the keeper assembly 44.

Coil springs 56, 58 surround the posts 30, 32 and act between the base 22 and bodies 46,48 to bias the keeper assembly 44 towards its first position. In the first position, a shoulder 60 on the body 46 captively presses the main body 40 of the medical instrument 12 against the seating surface 36. A shoulder 60' cooperates with the seating surface 36' of like configuration on the body 48 and post 32 to captively hold the main body 40 of the medical instrument 12. Accordingly, the main body 49 spans between the bodies 46, 48 and is cooperatively supported thereby so that the medical instrument 12 is consistently and stably maintained upon the support 10 in the operative position.

A single post with a wider seating surface, for additional stability, could be used in place of the multiple post arrangement.

By making the seating surfaces 36, 36' U-shaped, the same captive action for medical instruments having different diameters can be realized. An optional gripping element 62 can be provided on the shoulder 60 and corresponding shoulder 60' on the bodies 46, 48 to enhance the captive force between the shoulders 60, 60' and seating surfaces 36, 36'. For example, the gripping element 62 could be a compressible material, or ribs which produce a gripping effect.

The connector 50 has a sufficient length to allow a plurality of fingers, and in this case the user's entire hand 64, to be placed thereagainst to facilitate depression of the keeper assembly 44 against the force of the springs 56, 58 and thereby changing of the keeper assembly 44 from the first position into the second position. The arrows 66 indicate the direction of keeper assembly movement to change the keeper assembly 44 from the first position into the second position. Once this is accomplished, entryways 68, 68' to the seating surfaces 36, 36' are exposed to allow the main body 40 of the medical instrument 12 to be repositioned to allow the medical instrument 12 to be selectively placed in the operative position and fully separated from the support 10 by movement through the entryways 68, 68'. With the keeper assembly 44 in the second position, the medical instrument 12 can be lowered sufficiently to clear the ends 70, 70', whereupon it can be fully separated from the support 10 in the direction indicated by the arrows 74.

To facilitate replacement of the medical instrument 12 into the operative position, the body 46 is formed with a contoured outer surface 76. The outer surface 76 has a constant diameter midportion 78 which blends into a larger diameter portion 80 at the shoulder 60. The diameter increases gradually and smoothly from the midportion 78 to the larger diameter portion 80 so that the medical instrument 12 can be guided therealong, as shown in phantom in FIG. 3, in a vertical direction as indicated by the double-headed arrow A.

A portion 84 of the post 30 at the free end 70 extends further radially from the central axis 49 of the post 30 so as to intercept the medical instrument 12 being slid along the outer surface 76 towards the seating surface 36. The body 48 and post 32 are similarly configured to likewise perform a guiding function.

With the keeper assembly 44 slightly depressed from the first position towards the second position, the medical instrument 12 can be directed upwardly along the bodies 46, 48 and guided thereby up to and past the shoulders 60, 60' into the operative position against the seating surfaces 36,36', whereupon release of the keeper assembly 44 allows the keeper assembly 44 to be driven back into the first position to thereby captively hold the medical instrument 12.

The medical instrument 12 shown is but exemplary of the many types of medical instruments that could be used in conjunction with the inventive support 10. In this case, the medical instrument 12 is a commercially available needle holding mechanism. With the medical instrument 12 shown, compressing the spaced portions 86, 88 of a U-shaped grip 90 in an operator's hand 64 retracts a needle holding element 92 which allows placement therein of the needle 16, previously described. The working end 20 could likewise be used to facilitate knot tying, or other operations.

Virtually any type of instrument capable of being retained by the support 10 can be used in conjunction therewith. Laparoscopic instruments are particularly suitable for use with the support 10 given their substantial length and uniform diameter main body portion.

The foregoing disclosure of specific embodiments is intended to be illustrative of the broad concepts comprehended by the invention.

What is claimed is:

1. In combination:
a) a medical instrument having a main body; and
b) a support comprising:
a base;
a seating assembly on the base comprising a first seating surface against which the medical instrument abuts with the medical instrument in an operative position; and
a keeper assembly mounted for guided movement relative to the base between i) a first position wherein the keeper assembly directly abuts to the medical instrument in the operative position and thereby maintains the medical instrument in the operative position and ii) a second position wherein the medical instrument can be removed from the operative position.

2. The combination according to claim 1 wherein the base comprises a flat surface which can be placed facially against a subjacent surface.

3. The combination according to claim 1 wherein the first seating surface is fixed relative to the base.

4. In combination:
a) a medical instrument having a main body; and
b) a support comprising:
a base;
a seating assembly on the base comprising a first seating surface against which the medical instrument abuts with the medical instrument in an operative position; and
a keeper assembly mounted for guided movement relative to the base between i) a first position wherein the keeper assembly maintains the medical instrument in the operative position and ii) a second position wherein the medical instrument can be removed from the operative position,
wherein the seating assembly comprises a first post projecting from the base, the first seating surface is U-shaped, and the keeper assembly comprises a first body with a first shoulder that abuts to the medical instrument in the operative position with the keeper assembly in the first position.

5. The combination according to claim 4 wherein the first body and first post are movable guidingly, one inside the other.

6. The combination according to claim 4 wherein the U-shaped seating surface opens in a first direction, the first body has an outer surface with a central axis and a diameter, and the diameter of the outer surface varies smoothly so that the medical instrument can be guided against the outer surface oppositely to the first direction up to and past the first shoulder to against the first U-shaped seating surface.

7. The combination according to claim 6 wherein the first U-shaped seating surface has a portion that extends radially from the central axis further than the outer surface at the first shoulder so that as the medical instrument moves against the outer surface oppositely to the first direction up to and past the first shoulder, the medical instrument encounters the portion of the first U-shaped seating surface.

8. In combination:
a) a medical instrument having a main body; and
b) a support comprising:
a base;
a seating assembly on the base comprising a first seating surface against which the medical instrument abuts with the medical instrument in an operative position; and
a keeper assembly mounted for guided movement relative to the base between i) a first position wherein the keeper assembly maintains the medical instrument in the operative position and ii) a second position wherein the medical instrument can be removed from the operative position,
wherein the seating assembly comprises first and second posts each projecting from the base, the first seating surface is U-shaped, the seating assembly further comprising a U-shaped second seating surface against which the main body of the medical instrument abuts with the medical instrument in the operative position on the support, and the keeper assembly comprises a first body with a first shoulder that abuts to the medical instrument in the operative position with the keeper assembly in the first position and a second body with a second shoulder that abuts to the medical instrument in the operative position with the keeper assembly in the first position.

9. The combination according to claim 8 wherein there is a connector connected between the first and second bodies so that the connector and first and second bodies move as one piece as the keeper assembly changes between the first and second positions.

10. The combination according to claim 9 wherein the first body and first post are movable guidingly one inside the other and the second body and second post are movable guidingly one inside the other as the keeper assembly changes between the first and second positions.

11. In combination:
   a) a medical instrument having a main body; and
   b) a support comprising:
      a base;
      a seating assembly on the base comprising a first seating surface against which the medical instrument abuts with the medical instrument in an operative position; and
      a keeper assembly mounted for guided movement relative to the base between i) a first position wherein the keeper assembly maintains the medical instrument in the operative position and ii) a second position wherein the medical instrument can be removed from the operative position,
      wherein the keeper assembly is biased towards the first position.

12. The combination according to claim 11 wherein the keeper assembly is biased by a coil spring that surrounds the first post and acts between the base and the first body.

13. A method of using a medical instrument having a main body, said method comprising the steps of:

providing a support having a base, a seating assembly having a U-shaped seating surface, and a keeper assembly with a first shoulder that is movable guidingly relative to the base between first and second positions;

placing the keeper assembly in the second position;

directing the main body of the medical instrument against the seating surface to thereby place the medical instrument in an operative position;

with the medical instrument in the operative position changing the keeper assembly into the first position so that the first shoulder on the keeper assembly maintains the medical instrument in the operative position; and with the medical instrument maintained in the operative position, performing an operation on the medical instrument.

14. The method of using a medical instrument according to claim 13 wherein the medical instrument has a working end and the step of performing an operation comprises one of a) forming a knot at the working end and b) placing an element at the working end.

* * * * *